United States Patent [19]

Dillard et al.

[11] 4,171,361
[45] Oct. 16, 1979

[54] 1-SUBSTITUTED-3-AMINO-6,7-DIALKOXY-1H-1,2,4-BENZOTHIADIAZINE-1-OXIDES

[75] Inventors: Robert D. Dillard, Zionsville; Donald E. Pavey, Bargersville, both of Ind.

[73] Assignee: Eli Lilly and Company, Indianapolis, Ind.

[21] Appl. No.: 783,125

[22] Filed: Mar. 31, 1977

[51] Int. Cl.² .................... A61K 31/54; A61K 31/55; C07D 417/04; C07D 419/14
[52] U.S. Cl. .................... 424/246; 424/232; 544/9; 544/12; 260/243.3; 260/326.4; 260/340.5 R; 260/453 AR; 260/575; 260/609 R; 568/587
[58] Field of Search .................... 260/243.3; 544/12 (U.S. only), 9 (U.S. only), 9, 12; 424/246

[56] References Cited

U.S. PATENT DOCUMENTS

| 3,933,805 | 1/1976 | Cohnen ............................ 260/243 D |
| 3,957,769 | 5/1976 | Sowinski et al. ................ 260/243 D |

FOREIGN PATENT DOCUMENTS 2530792  1/1977  Fed. Rep. of Germany ...... 260/243 D

OTHER PUBLICATIONS

Stoss et al. II, Ber. Deut. Chem., vol. 109, pp. 2097–2106 (1976).

Primary Examiner—Alton D. Rollins
Attorney, Agent, or Firm—James L. Rowe; Arthur R. Whale

[57] ABSTRACT

1-Substituted-3-amino-6,7-dialkoxy-1H-1,2,4-benzothiadiazine-1-oxides, useful as hypotensive agents.

13 Claims, No Drawings

1-SUBSTITUTED-3-AMINO-6,7-DIALKOXY-1H-1,2,4-BENZOTHIADIAZINE-1-OXIDES

BACKGROUND OF THE INVENTION 1,2,4-Benzothiadiazine-1-oxides are known in the art. For example, U.S. Pat. No. 3,936,977 discloses 1-phenyl (or substituted phenyl)-1H-1,2,4-benzothiadiazine-3(4H)-ones bearing a substituent on the C-3 nitrogen and permissible substituents in the phenyl ring of the benzothiadiazine including alkoxy. The compounds disclosed therein are stated to be central nervous system depressants and diuretics. U.S. Pat. No. 3,957,769 discloses 1-phenyl (or substituted phenyl) 3-amino (or alkylamino or dialkylamino)-1H-1,2,4-benzothiadiazine-1-oxides which may permissibly be substituted in the phenyl ring of the benzothiadiazine with, among other groups, an alkoxy group. These compounds are also said to be central nervous system depressants and diuretics. Specifically disclosed are 7-methoxy-3-methylamino-1-phenyl-1,2,4-benzothiadiazine-1-oxide and 6-methoxy-3-methylamino-1-phenyl-7-sulfamyl-1,2,4-benzothiadiazine-1-oxide. U.S. Pat. No. 3,933,805 disclosed 1-phenyl (or substituted phenyl) 3-dialkylaminomethyl-1H-1,2,4-benzothiadiazine-1-oxides permissibly substituted with methoxy in the phenyl ring of the benzothiadiazine molecule. The compounds are said to be anti-hypertensives. Stoss and Satzinger, *Chem. Ber.*, 109, 2097 (1976) prepared 1-phenyl or 1-methyl-3-amino-1H-1,2,4-benzothiadiazine-1-oxides containing a methyl or chloro substituent in the benzene ring portion of the benzothiadiazine ring. An imino group substituted at the 3 position of the benzothiadiazine ring is illustrated in Tables 1 and 2 of the article. Cohnen and Mahnke, *Chem. Ber.*, 105, 757, (1972) described on page 758, compound 7jA which is 1-phenyl-3-methylaminomethyl-7-chloro-1H-1,2,4-benzothiadiazine-1-oxide. The compounds described therein were employed as intermediates for the preparation of Librium-like drugs.

1-Substituted-6,7-dialkoxy-(methoxy, ethoxy, or methylene dioxy)-1H-1,2,4-benzothiadiazine-1-oxides carrying a direct attached amino group in the 3-position have not been disclosed, either generically or specifically, in the prior art.

SUMMARY OF THE INVENTION

This invention provides 1-substituted-6,7-dialkoxy-1H-1,2,4-benzothiadiazine-1-oxides of the formula:

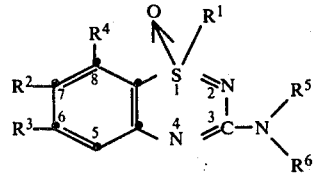

wherein $R^1$ is $C_1$–$C_3$ alkyl or

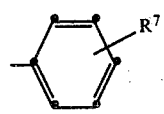

$R^7$ is chloro, bromo, fluoro, methyl, ethyl, methoxy, ethoxy or trifluoromethyl;

$R^2$ and $R^3$ when taken singly are methoxy or ethoxy and when taken together are methylene deoxy, $R^4$ is H or methoxy, $R^5$ is, when taken singly, H or $C_1$–$C_5$ alkyl, $R^6$ when taken singly is $C_1$–$C_5$ alkyl, or

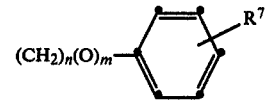

wherein n is 1 or 2, and m is 0 or 1, $R^5$ and $R^6$, when taken together with the nitrogen to which they are attached form a piperidino group

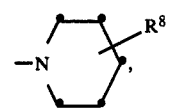

a piperazino group

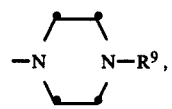

a homopiperazino group

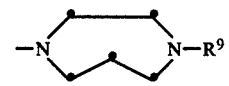

or a 4-hydroxy-4-phenylpiperidino group, wherein $R^8$ is a substituent in the 3 or 4 position of the piperidine ring chosen from the group consisting of H, OH, lower alkanoyloxy, lower alkoxy, hydroxy lower alkyl,

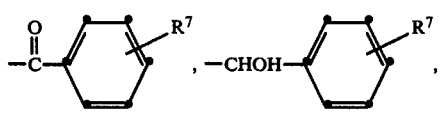

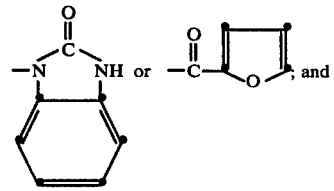

$R^9$ is $C_1$–$C_3$ alkyl,

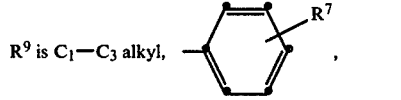

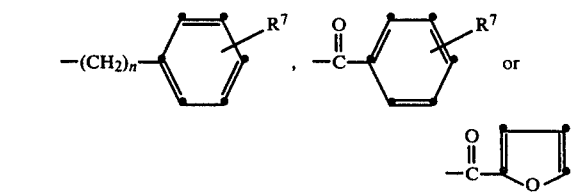

and pharmaceutically-acceptable acid addition salts thereof.

In the above formula, when $R^1$ or $R^9$ is $C_1$-$C_3$ alkyl, it can be methyl, ethyl, isopropyl, or n-propyl. When $R^5$ or $R^6$ are $C_1$-$C_5$ alkyl, they can be the same groups enumerated for $R^1$ when it was $C_1$-$C_3$ alkyl, plus such radicals as n-butyl, iso-butyl, sec-butyl, n-amyl, iso-amyl, and the like. When $R^8$ is lower alkanoyloxy, the term includes acetoxy, propionoxy and butyroxy. The term, lower alkoxy as used herein includes methoxy, ethoxy or propoxy and the term hydroxy lower alkyl includes hydroxymethyl, α-hydroxyethyl, β-hydroxyethyl, β-hydroxypropyl etc.

A preferred group of compounds of this invention are those in which $R^1$ is $C_1$-$C_3$ alkyl, preferably methyl, $R^4$ is H, $R^2$ and $R^3$ are both methoxy, and $R^5$ and $R^6$ have the same scope as above.

The pharmaceutically-acceptable acid addition salts of this invention include salts derived from inorganic acids such as: hydrochloric acid, nitric acid, phosphoric acid, sulfuric acid, hydrobromic acid, hydriodic acid, nitrous acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Illustrative bases coming within the scope of this invention include:

1-ethyl-6,7-diethoxy-3-isoamylamino-1H-1,2,4-benzothiadiazine-1-oxide, 1-isopropyl-6,7-diethoxy-8-methoxy-3-(2-bromobenzyl)amino-1H-1,2,4-benzothiadiazine-1-oxide, 1-p-methoxyphenyl-6,7-methylenedioxy-3-p-methoxyphenylbenzylamino-1H-1,2,4-benzothiadiazine-1-oxide, 1-m-tolyl-6,7,8-trimethoxy-3-[2-(o-anisyl)ethyl]amino-1H-1,2,4-benzothiadiazine-1-oxide, 1-(2-fluorophenyl)-6,7-methylenedioxy-3-[4-(p-anisyl)-piperazino]-1H-1,2,4-benzothiadiazine-1-oxide, 1-(m-tolyl)-6,7-diethoxy-3-(4-propionoxypiperidino)-1H-1,2,4-benzothiadiazine-1-oxide, 1-(p-chlorophenyl)-6,7-dimethoxy-3-[4-(α-hydroxy-p-chlorobenzyl)piperidino]-1H-1,2,4-benzothiadiazine-1-oxide, 1-(p-ethoxyphenyl)-6,7-dimethoxy-3-[4-(p-bromobenzoyl)piperidino]-1H-1,2,4-benzothiadiazine-1-oxide, 1-(m-fluorophenyl)-6,7-dimethoxy-3-(4-n-propoxypiperidino)-1H-1,2,4-benzothiadiazine-1-oxide, 1-(4-bromophenyl)-6,7-diethoxy-3-[4-(α-hydroxybenzyl)piperidino]-1H-1,2,4-benzothiadiazine-1-oxide, 1-(4-trifluoromethylphenyl)-6,7-methylenedioxy-3-(4-hydroxymethylpiperidino)-1H-1,2,4-benzothiadiazine-1-oxide, 1-(4-ethylphenyl)-5,6,7-trimethoxy-3-[4-(β-hydroxyethyl)piperidino]-1H-1,2,4-benzothiadiazine-1-oxide, 1-(2-trifluoromethylphenyl)-6,7-diethoxy-3-[4-(α-hydroxypropyl)piperidino]-1H-1,2,4-benzothiadiazine-1-oxide, 1-ethyl-6,7-diethoxy-3-(4-ethoxy-piperidino)-1H-1,2,4-benzothiadiazine-1-oxide, 1-methyl-6,7-dimethoxy-3-[4-(β-hydroxy-α-methylethyl)piperidino]-1H-1,2,4-benzothiadiazine-1-oxide and the like.

The compounds of this invention, either as such are in the form of an acid addition salt thereof are useful in lowering blood pressure. Although they demonstrate this useful activity in the laboratory in both normotensive and spontaneously hypertensive mammals, the compounds would be employed to lower blood pressure of mammals having an elevated blood pressure. Thus, this invention also provides a method of lowering blood pressure in a mammal having an elevated blood pressure and in need of treatment, employing a hypotensive dose of a compound according to the above formula. Particularly useful hypotensive agents of this invention are those which are members of the preferred group of compounds referred to above. The pharmaceutically-acceptable salts of these compounds are, of course, equally useful in treating hypertension.

In carrying out the therapeutic method of the present invention, it is generally preferred to employ a composition comprising the active agent and one or more adjuvants suited to the particular route of administration. Compositions for oral administration may be either solid; e.g., capsules, tablets, pills, powders, etc., or liquid; e.g., emulsions, solutions, suspensions, syrups, elixirs, etc. combined with conventional adjuvants. In the case of solid formulations, suitable adjuvants include inert substances such as sucrose, lactose, and starch. In the case of liquid formulations, suitable adjuvants include water, mineral oil, etc. When an aqueous solution is desired, an acid addition salt is conveniently employed. Either solid or liquid formulations can include lubricating agents, wetting agents, emulsifying and suspending agents, preserving agents, sweetening agents or flavoring agents.

In the instance of parenteral administration, the compounds of the present invention are formulated in a suitable sterile, injectable liquid. For example, a pharmaceutically-acceptable acid-addition salt formed with a non-toxic acid is used in an isotonic salt solution for I.V. or other injection route. Oral administration is generally preferred. An acceptable formulation for oral use is a pharmaceutical preparation in dosage unit form adapted for administration to obtain a hypotensive effect, comprising, per dosage unit, an effective non-toxic amount within the range from about 0.01 to about 100 milligrams of one or more of the compounds of this invention.

The compounds of this invention are prepared according to the following reaction scheme:

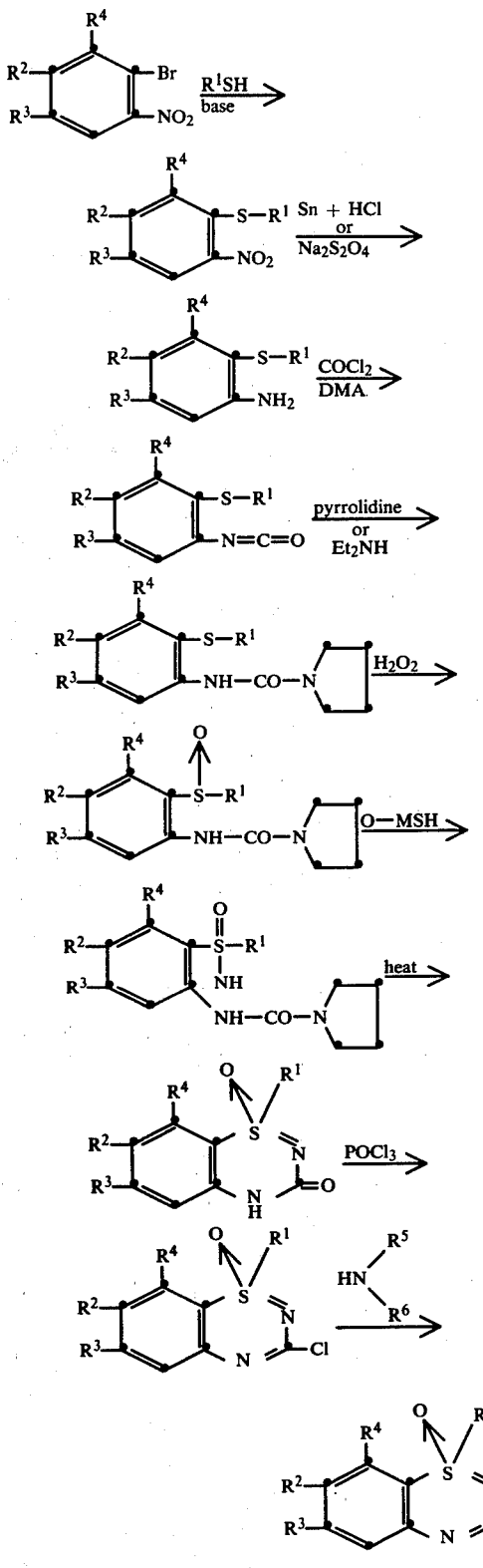

Reaction Scheme wherein $R^1$, $R^2$, $R^3$, $R^4$, $R^5$ and $R^6$ have the meaning heretofore designated.

In carrying out the reactions symbolically illustrated in the above Reaction Scheme, a suitably substituted o-bromonitrobenzene (I) is reacted with a mercaptan $R^1SH$ to yield the corresponding ortho-alkyl (or phenyl) mercaptonitrobenzene (II). Reduction of the nitro group, as with tin in hydrochloric acid or other suitable reducing agent, gives the ortho-alkyl (or aryl)-mercaptoaniline (III). Reaction of the aniline group with phosgene in the presence of dimethylaniline (DMA) gives the corresponding isocyanate (IV) which, isocyanate upon reaction with a secondary amine such as pyrrolidine or diethylamine, yields a substituted urea (V). Oxidation of the urea with peroxide yields the sulfoxide (VI). Reaction of this compound with o-mesitylenesulfonylhydroxylamine forms the substituted sulfoximine compound (VII). This compound cyclizes with heat to yield the 3-oxobenzothiadiazine-1-oxide (VIII). Treatment of 3-oxo compound with phosphorous oxychloride or other suitable chlorinating agents yields the substituted 3-chlorobenzothiadiazine-1-oxide (IX). The labile chlorine of this derivative reacts readily with secondary or primary amines of the formula $HN-R^5R^6$ to yield the compounds of this invention (X).

Compounds having a 1-substituted-1H-1,2,4-benzothiadiazine-1-oxide ring system, including both the compounds of this invention and intermediates useful in their preparation, contain an assymetric center. This center is the tetrahedral sulfur atom which is attached to four different groups, including the oxide group. Intermediate sulphoximide compounds also contain a tetrahedral assymetric sulfur atom and are therefore chiral. Resolution of such chiral molecules into optically-active enantiomers can be accomplished by procedures available from the art.

Structures VII thru X of the above Reaction Scheme represent both enantiomers resulting from chiral sulfur atoms present therein. It is not known whether one or both enantiomers have the pronounced hypotensive activity set forth in Table I, etc. and a racemate containing one or more active enantiomers is also useful as a hypotensive agent.

This invention is further illustrated by the following specific examples.

EXAMPLE 1

Preparation of 3-Bromo-4-nitroveratrole 100 g. of 4-bromoveratrole were added in dropwise fashion with stirring to 750 ml. of nitric acid (Sp. Gr. 1.42) over a 40 minute period. The temperature was maintained in the range $-8°$ C. to $-4°$ C. with external cooling consisting of an ice-ethanol bath. After the addition had been completed, the stirring was continued for another 10 minutes with cooling. 3-Bromo-4-nitroveratrole formed in the above reaction precipitated after diluting the reaction mixture with 2500 ml. of water. The precipitate was separated by filtration, and the filter cake washed with water. Recrystallization of the filter cake from about 2.5 l. of ethanol yielded 3-bromo-4-nitroveratrole, a light yellow product, which melted at $120°-122°$ C. Yield=83.4 g.

Analysis Calc.: C, 36.67; H, 3.08; N, 5.34. Found: C, 36.44; H, 3.05; N, 5.97.

EXAMPLE 2

Preparation of 3-Methylthio-4-nitroveratrole

A reaction mixture containing 21 g. of potassium carbonate, 25 g. of methanethiol, and 30 ml. of ethanol was cooled in an ice-water bath. 33.5 g. of 3-bromo-4-nitroveratrole were added thereto. The reaction mixture was stirred for 1 hour under cooling and was then allowed to warm up to ambient temperature, at which temperature it was stirred for an additional 24 hours. 3 l. of water were then added and the resulting precipitate of 3-methylthio-4-nitroveratrole formed in the above reaction was separated by filtration. The filter cake was recrystallized from a benzene-ethanol solvent mixture to yield yellow crystals melting at 137°–140° C. (weight=22.8 g)

Analysis Calc.: C, 47.15; H, 4.84; N, 6.11. Found: C, 47.38; H, 4.97; N, 6.16.

An additional 3.1 g. of 3-methylthio-4-nitroveratrole were recovered from the mother liquor.

EXAMPLE 3

Preparation of 2-Methylthio-4,5-dimethoxyaniline

A reaction mixture was prepared containing 107.1 g. of 200 mesh metallic tin, 330 ml. of glacial acetic acid, and 50 ml. of 12 N aqueous hydrochloric acid. 68.7 g. of 3-methylthio-4-nitroveratrole were added thereto in 4 portions over a 20 minute period. After the addition had been completed, the reaction temperature had risen to 105° C. An additional 300 ml. of 12 N aqueous hydrochloric acid were added thereto over a 10 minute period. The temperature was maintained in the range 100°–105° C. for about 1.5 hours. The reaction mixture was then cooled in an ice-water bath, made strongly basic with 50 percent aqueous sodium hydroxide and diluted with 5 volumes of water. The aqueous layer was extracted three times with 2 liter portions of ether. The ether extracts were combined, dried, and the ether removed therefrom in vacuo. The resulting residue comprising 2-methylthio-4,5-dimethoxyaniline formed in the above reduction melted at 72°–4° C. after recrystallization from a benzene-hexane solvent mixture. Yield=37 g. An additional 10 g. were obtained from mother liquors.

Analysis Calc.: C, 54.25; H, 6.58; N, 7.03. Found: C, 54.13; H, 6.58; N, 7.05.

EXAMPLE 4

Alternate Preparation of 2-Methylthio-4,5-dimethoxyaniline

A reaction mixture was prepared containing 68.7 g. of 3-methylthio-4-nitroveratrole, 261 g. sodium dithionite ($Na_2S_2O_4$), 1500 ml. of ethanol and 2250 ml. of water. The reaction mixture was heated at reflux temperature for about 1 hour and then cooled. The reaction mixture was then made basic with potassium carbonate and the resulting alkaline solution concentrated in vacuo to one-half its original volume. The aqueous solution was extracted twice with 2 l. portions of ether. The ether extracts were combined, dried, and the ether removed therefrom by evaporation in vacuo. The solid residue, comprising 2-methylthio-4,5-dimethoxy aniline formed in the above reaction, was recrystallized from a benzene-hexane solvent mixture to yield 33.6 g. of crystalline material melting at 69°–72° C.

EXAMPLE 5

Preparation of N-pyrrolidinylcarbonyl-2-methylthio-4,5-dimethoxyaniline

A solution of 24 g. of phosgene in toluene was added rapidly to a solution of 58.1 g. of N,N-dimethylaniline in 500 ml. of toluene, which solution has been previously cooled to about 0° C. with an ice-water bath. After stirring the resulting solution for about five minutes, a solution of 39.8 g. of 2-methylthio-4,5-dimethoxyaniline in 350 ml. of toluene was added on dropwise fashion over a 30 minute period to the cooled, stirred reaction mixture. The reaction mixture was allowed to warm to ambient temperature, at which temperature it was stirred for an additional four hours. The reaction mixture was then filtered, and the filtrate concentrated under reduced pressure to a thick oil. The oil was dissolved in 1 l. of acetonitrile and 50 ml. of pyrrolidine were added thereto. This new reaction mixture was stirred for about 20 hours, after which time it was concentrated under reduced pressure to a thick oil. The residual oil was dissolved in 1 l. of methylene chloride. The methylene chloride solution was washed twice with 5 percent aqueous hydrochloric acid and once with water. The methylene chloride solution was then dried and the solvent removed therefrom in vacuo, leaving a solid residue comprising N-pyrrolidinylcarbonyl-2-methylthio-4,5-dimethoxyaniline. Recrystallization of the solid from a benzene-hexane solvent mixture yield crystalline material melting at 141°–3° C. (91 percent yield).

Analysis Calc.: C, 56.74; H, 6.80; N, 9.45. Found: C, 56.73; H, 6.52; N, 9.77.

EXAMPLE 6

Preparation of N-pyrrolidinylcarbonyl-2-methylsulfinyl-4,5-dimethoxyaniline

A reaction mixture containing 52 g. of N-pyrrolidinylcarbonyl-2-methylthio-4,5-dimethoxyaniline 19.8 ml. of 31 percent aqueous hydrogen peroxide and 1 l. of glacial acetic acid was stirred for about 20 hours at ambient temperature. The reaction mixture was then concentrated under reduced pressure to a residual wax. The residue was dissolved in 1 l. of methylene chloride and the methylene chloride layer washed twice with water and then dried. Removal of the methylene chloride in vacuo yielded a residue comprising N-pyrrolidinylcarbonyl-2-methylsulfinyl-4,5-dimethoxyaniline which, after recrystallization from a benzene-hexane solvent mixture, yielded material melting at 124°–7° C. (80 percent yield).

Analysis Calc.: C, 53.83; H, 6.45; N, 8.97. Found: C, 53.90; H, 6.34; N, 8.89.

EXAMPLE 7

Preparation of S-methyl-S-[2-(pyrrolidinylcarbonylamino)-4,5-dimethoxyphenyl]sulfoximine A reaction mixture containing 51.7 g. of N-pyrrolidinylcarbonyl-2-methylsulfinyl-4,5-dimethoxyaniline and 0.48 mole of O-mesitylenesulfonylhydroxylamine (prepared by the procedure of Tamura et al., *J. Org. Chem.* 38, 1239, 1973) and 1 l. of acetonitrile was stirred for 48 hours at ambient temperature. The reaction was then concentrated at reduced pressure and the resulting residue dissolved in 2 l. of methylene chloride. The methylene chloride solution was shaken with 1500 ml. of cold water containing 200 ml. of 14 N aqueous ammonium hydroxide. The organic layer was separated, washed with water, and dried. Evaporation of the methylene chloride solvent in vacuo yielded a residue comprising S-methyl-S-[2-(pyrrolidinylcarbonylamino)-4,5-dimethoxyphenyl]sulfoximine. Crystallization of the residue from a chloroform-cyclo hexane solvent mixture yielded 38 g. of crystalline material (70 percent yield) melting at 312°–314° C.

Analysis Calc.: C, 51.36; H, 6.47; N, 12.83. Found: C, 51.16; H, 6.72; N, 12.75.

EXAMPLE 8

Preparation of 6,7-Dimethoxy-1-methyl-1H-1,2,4-benzothiadiazine-3(4H)-one-1-oxide A solution was prepared from 42.8 g. of S-methyl-S-[2-(pyrrolidinylcarbonylamino)-4,5-dimethoxyphenyl]-sulfoximine and 1 l. of bromobenzene. The reaction mixture was heated to reflux temperature for three hours, and was then cooled and filtered. The filter cake was dissolved in 700 ml. of chloroform. The chloroform solution was cooled and 6,7-dimethoxy-1-methyl-1H-1,2,4-benzothiadiazine-3(4H)-one-1-oxide formed in the above reaction crystallized therefrom. The crystalline material melted at 326°–328° C. (91 percent yield).

Analysis Calc: C, 46.87; H, 4.72; N, 10.93. Found: C, 46.63; H, 4.61; N, 10.63.

EXAMPLE 9

Alternate Preparation of 6,7-Dimethoxy-1-methyl-1H-1,2,4-benzothiadiazine-3(4H)-one-1-oxide The procedure of examples 5–8 was followed except that diethylamine was reacted with 2-methylthio-4,5-dimethoxyphenylisocyanate (formed from the reaction of 2-methylthio-4,5-dimethoxyaniline and phosgene in the presence of N,N-dimethylaniline).

The resulting product, N-[2-methylthio-4,5-dimethoxyphenyl]-N',N'-diethylurea was oxidized with hydrogen peroxide to yield N-[2-methylsulfinyl-4,5-dimethoxyphenyl]-N',N'-diethylurea. Reaction of this compound with O-mesitylenesulfonylhydroxylamine yielded S-methyl-S-[2-diethylaminocarbonylamino-4,5-dimethoxyphenyl]sulfoximine. Heating the sulfoximine yielded 6,7-dimethoxy-1-methyl-1H-1,2,4-benzothiadiazine-3(4H)-one-1-oxide melting at 333°–335° C. Total yield was 59 percent based on 2-methylthiol-4,5-dimethoxyaniline.

EXAMPLE 10

Preparation of 3-Amino-6,7-dimethoxy-1-methyl-1H-1,2,4-benzothiadiazine-1-oxides A reaction mixture was prepared containing 2.6 g. of 6,7-dimethoxy-1-methyl-1H-1,2,4-benzothiadiazine-3(4H)-one-1-oxide, 25 ml. of phosphorous oxychloride and ½ ml. of water. The reaction mixture was heated to refluxing temperature for about 3 hours and was then poured over 200 g. of ice with stirring. The aqueous layer was extracted with chloroform. The chloroform extract was separated and and dried, and the chloroform removed therefrom by evaporation in vacuo. The residue, a tan solid comprising 6,7-dimethoxy-1-methyl-3-chloro-1H-1,2,4-benzothiadiazine-1-oxide was dissolved in 100 ml. of acetonitrile. Five grams of 4-phenylpiperidine were added. The resulting reaction mixture was heated at refluxing temperature for about 20 hours. The volatile constituents were removed under reduced pressure yielding a solid residue comprising 3-(4-phenylpiperidino)-6,7-dimethoxy-1-methyl-1H-1,2,4-benzothiadiazine-1-oxide formed in the above reaction. The residue was dissolved in 1 l. of methylene chloride, the organic layer was washed with a concentrated aqueous potassium carbonate solution, and then dried. Removal of the solvent in vacuo yielded a crystalline residue.

The corresponding hydrochloric salt was prepared using ethanolic hydrogen chloride to yield 3-(4-phenylpiperidino)-6,7-dimethoxy-1-methyl-1H-1,2,4-benzothiadiazine-1-oxide hydrochloride melting at 216°–218° C. (55 percent yield).

Analysis Calc.: C, 57.85; H, 6.01; N, 9.64. Found: C, 57.62; H, 5.79; N, 9.94.

Table 1, below gives the melting point and analytical chemical data for a series of 3-amino compounds prepared by substituting different amines for 4-phenylpiperidine in the above example. In the table, column 1 gives the name of the amine substituent, column 2, the melting point, column 3, 4 and 5, the calculated carbon, hydrogen and nitrogen analyses and columns 6, 7, and 8, the found carbon hydrogen and nitrogen values.

The compounds of this invention, including those prepared by the method of Example 10, whose physical characteristics are set forth in Table 1 below, are hypotensive agents. They manifest their hypotensive activity by demonstrating an ability to reduce the blood pressure of normotensive rabbits. The test procedure employed is as follows:

Male white rabbits weighing approximately 2.5–3.5 kg. are used. These animals have chronic indwelling arterial cannulae prepared as follows: The rabbits are anesthetized with secobarbital (30 mg/kg i.v.). An incision is made along the linea alba at the approximate level of the bifurcation of the abdominal aorta. A tygon cannula is inserted into the aorta at its bifurcation and anchored so that the tip of the cannula is just distal to the renal artery. The distal end of the cannula is looped, anchored to the posterior abdominal wall, and passed through muscle wall and run subcutaneously rostral, and exteriorized at the nape of the neck. The cannula is kept filled with heparin (1000 units/ml) and, when not in use, is plugged with a stylet. Systolic, diastolic and mean blood pressure in rabbits so prepared is measured by direct recording. The drug under evaluation is administered to the test rabbit at a predetermined dose level with a 0.2 ml/kg. injection volume intravenously via a major ear vein. While the blood pressure is being recorded, heparin is infused through the transducer and into the artery at a rate of 0.01 ml/min. using a Harvard Apparatus infusion pump. This infusion serves two purposes (1) it insures a clot-free period for recording and (2) results in a more stable baseline for pressure recording.

The control period starts 30 min. after the rabbits have been placed in their stocks. The control values are taken after the 30 minutes "accomodation" period. The drug is then administered intravenously and readings taken at set intervals terminating at 120 min. post-dosing. The data are analyzed using a Student t test.

In Table 1, which follows, in column 9, there is given the lowest dose level in mg/kg. of rabbit body weight which produced a statistically significant lowering of blood pressure for the drug named in column 1.

TABLE 1

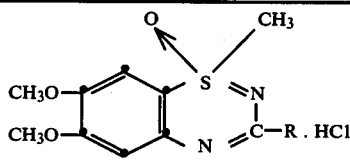

| R | Melting Point °C. | Analysis Calcd. C | H | N | Found C | H | N | Hypotensive Dose |
|---|---|---|---|---|---|---|---|---|
| methyl-NH | 216–218 | 43.21 | 5.27 | 13.74 | 43.24 | 5.53 | 13.87 | 0.08 |
| Isopropyl-NH | 226–228 | 46.77 | 6.04 | 12.59 | 46.53 | 5.97 | 12.30 | 2.5 |
| n-Butyl-NH | 212–214 | 48.34 | 6.37 | 12.08 | 48.12 | 6.13 | 11.93 | 1.25 |
| Phenyl-NH | 245–247 | 52.24 | 4.93 | 11.42 | 52.22 | 4.73 | 11.17 | 0.5 |
| Benzyl-NH | 205–207 | 53.61 | 5.03 | 11.03 | 53.46 | 5.14 | 10.97 | 1.25 |
| β-Phenylethyl-NH | 234–236 | 54.61 | 5.60 | 10.61 | 54.33 | 5.7 | 10.69 | 1.25 |
| β-(o-Anisyloxy)ethyl-NH | 200–202 | 51.64 | 5.47 | 9.51 | 51.37 | 5.42 | 9.21 | 5.0 |
| Dimethyl-N | 234–236 | 45.07 | 5.67 | 13.14 | 45.35 | 5.45 | 12.95 | 0.125 |
| Diethyl-N | 210–212 | 48.34 | 6.37 | 12.08 | 48.31 | 6.10 | 11.84 | 0.04 |
| Di-n-propyl-N | 110–112 | 51.12 | 6.97 | 11.18 | 51.35 | 6.81 | 11.28 | 5.0 |
| Piperidino | 201–203 | 50.06 | 6.16 | 11.68 | 49.98 | 6.50 | 12.04 | 0.625 |
| 4-Phenylpiperidino | 216–218 | 57.85 | 6.01 | 9.64 | 57.62 | 5.79 | 9.94 | 0.16 |
| 4-(α-Hydroxybenzyl)-piperidino | 232–234 | 57.70 | 6.06 | 9.02 | 56.48 | 5.96 | 8.76 | 0.04 |
| 4-(1,3-Dihydro-2-oxo-1-benzamidazolyl)-piperidino | 243–245 | 53.71 | 5.33 | 14.23 | 53.44 | 5.66 | 13,98 | 1.25 |
| N'-methylpiperazino | 235–237 | 43.69 | 6.08 | 13.62 | 43.48 | 6.46 | 13.05 | 5.0 |
| N'-phenylpiperazino | 186–188 | 50.73 | 5.54 | 11.84 | 50.25 | 5.40 | 11.54 | 0.3125 |
| N'-benzylpiperazino | 243–245 | 51.74 | 5.99 | 11.49 | 52.14 | 6.34 | 11.40 | 5.0 |
| N'-benzoylpiperazino | 208–210 | 54.25 | 5.42 | 12.05 | 54.42 | 5.33 | 11.94 | 0.0312 |
| N'-(2-furoyl)piperazino | 242–245 | 50.16 | 5.10 | 12.32 | 50.12 | 5.33 | 12.42 | .008 |
| N'-(2-furoyl)-homo-piperazino | 206–208 | 51.22 | 5.37 | 11.95 | 51.45 | 5.66 | 11.68 | .025 |
| 4-Hydroxypiperidino | 209–210 | 47.93 | 5.90 | 11.18 | 48.16 | 6.08 | 11.25 | .625 |
| 4-Hydroxy-4-phenyl-piperidino | 222–224 | 55.81 | 5.80 | 9.30 | 55.62 | 5.74 | 9.20 | * |
| 4-Benzoylpiperidino | 220–222 | 56.95 | 5.65 | 9.00 | 56.72 | 5.88 | 8.88 | * |
| 3-Hydroxypiperidino | 162–168 | 47.93 | 5.90 | 11.18 | 47.77 | 5.72 | 10.94 | * |
| 4-Acetoxypiperidino | 210–212 | 48.86 | 5.79 | 10.05 | 48.83 | 5.79 | 9.89 | * |

*Not tested in normotensive rabbits but active in spontaneously hypertensive rats.

Each of the compounds prepared in Example 1 is a 1-methyl-6,7-dimethoxy derivative. The preparation of compounds according to the procedure of Example 1, in which the substituent in the 1 position is other than methyl, is illustrated below in Example 11.

EXAMPLE 11

Preparation of 1-Substituted-6,7-dimethoxy-3-substituted amino-1H-1,2,4-benzothiadiazine-1-oxides Following the procedure of Example 2, 3-bromo-4-nitroveratrole were reacted with phenylmercaptan, ethanethiol and isopropylthiol respectively to form the following compounds:

3-Phenylthio-4-nitroveratrole melting at 110°–112° C.
Analysis Calc.: C, 57.72; H, 4.50; N, 4.81. Found: C, 57.83; H, 4.80; N, 5.15.

3-Ethanethio-4-nitroveratrole melting at 145°–7° C.
Analysis Calc.: C, 49.37; H, 5.39; N, 5.76. Found: C, 49.15; H, 5.52; N, 5.62.

3-Isopropylthio-4-nitroveratrole melting at 107°–109° C.
Analysis Calc.: C, 51.35; H, 5.88; N, 5.44. Found: C, 51.16; H, 5.64; N, 5.45.

Following the procedure of Example 3, the nitro group in each of the above compounds was reduced to an amino group to yield the following compounds.

2-Phenylthio-4,5-dimethoxyaniline melting at 70°–74° C.
Analysis Calc.: C, 69.34; H, 5.79; N, 5.36. Found: C, 69.18; H, 6.06; N, 5.42.

2-Ethanethio-4,5-dimethoxyaniline boiling at 104°–113° C. at 0.05 mm/Hg
Analysis Calc.: C, 56.31; H, 7.09; N, 6.57. Found: C, 56.03; H, 5.89; N, 6.53.

2-Isopropylthio-4,5-dimethoxyaniline boiling at 106°–111° C. at 0.05 mm/Hg
Analysis Calc.: C, 58.12; H, 7.54; N, 6.16. Found: C, 58.30; H, 7.82; N, 6.08.

Following the procedure of Example 5, the above three anilines were reacted with phosgene in the presence of N,N-dimethylaniline to form the corresponding isocyanate. The isocyanates were in turn reacted with diethylamine to form the corresponding diethylurea. Reaction of the urea successively with hydrogen peroxide and O-mesitylenesulfonylhydroxylamine yielded the corresponding S-substituted-S-[2-(diethylaminocarbonylamino)-4,5-dimethoxyphenyl]sulfoximines, which compounds were in turn cyclized with heat to yield the corresponding 6,7-dimethoxy-1-substituted-1H-1,2,4-benzothiadiazine-3(4H)-one-1-oxides as follows.

1-Phenyl-6,7-dimethoxy-1H-1,2,4-benzothiadiazine-3(4H)-one-1-oxide melting at 245°–7° C.
Analysis Calc.: C, 56.59; H, 4.43; N, 8.80. Found: C, 56.83; H, 4.69; N, 8.55.

1-Ethyl-6,7-dimethoxy-1H-1,2,4-benzothiadiazine-3(4H)-one-1-oxide melting at 284°–6° C.
Analysis Calc.: C, 48.44; H, 5.22; N, 10.36. Found: C, 49.08; H, 5.10; N, 10.41.

1-Isopropyl-6,7-dimethoxy-1H-1,2,4-benzothiazine-3(4H)-one-1-oxide melting at 253°-5° C.

Analysis Calc.: C, 50.69; H, 5.67; N, 9.85. Found: C, 50.79; H, 5.74; N, 9.91.

Reaction of the 3-oxo compound with phosphorous oxychloride yielded the corresponding 3-chloro compound which, on reaction with 4-furoylpiperazine, yielded the following compounds:

1-Phenyl-3-[4-(2-furoyl)piperazino]-6,7-dimethoxy-1H-1,2,4-benzothiadiazine-1-oxide hydrochloride melting at 235°-7° C.

Analysis Calc.: C, 55.76; H, 4.87; N, 10.84. Found: C, 55.66; H, 5.19; N, 10.60.

1-Ethyl-3-[4-(2-furoyl)piperazino]-6,7-dimethoxy-1H-1,2,4-benzothiadiazine-1-oxide hydrochloride melting at 216°-18° C.

Analysis Calc.: C, 51.22; H, 5.37; N, 11.95. Found: C, 51.17; H, 5.28; N, 11.68.

1-Isopropyl-3-[4-(2-furoyl)piperazino]-6,7-dimethoxy-1H-1,2,4-benzothiadiazine-1-oxide hydrochloride melting at 210°-12° C.

Analysis Calc.: C, 52.22; H, 5.63; N, 11.60. Found: C, 51.95; H, 5.90; N, 11.51.

Variation of the groups in the 6,7 position of the benzothiadiazine ring to include ethoxy substituents or a methylene dioxy group occupying both 6 and 7 positions is accomplished by using starting materials already containing such groups as in the following example:

EXAMPLE 12

Preparation of 6,7-Substituted-1-methyl-3-substituted-1H-1,2,4-benzothiadiazine-1-oxides Following the procedure of Example 1, 3,4-diethoxybromobenzene and 3,4-methylenedioxybromobenzene were nitrated to yield the corresponding 6-nitro compound. The nitro compounds were reacted with methanethiol by the procedure of Example 2 to form the following compounds:

2-Methylthio-4,5-diethoxynitrobenzene melting at 105°-108° C.

Analysis Calc.: C, 51.35; H, 5.88; N, 5.44. Found: C, 51.37; H, 6.10; N, 5.67.

2-Methylthio-4,5-methylenedioxynitrobenzene melting at 195°-9° C.

Analysis Calc.: C, 45.07; H, 3.31; N, 6.57. Found: C, 45.20; H, 3.06; N, 6.53.

Reduction of these nitro compounds by the procedure of Example 3 yielded the following anilines:

2-Methylthio-4,5-diethoxyaniline boiling at 112°-115° C. at 0.02 mm/Hg

Analysis Calc.: C, 58.12; H, 7.54; N, 6.16. Found: C, 57.99; H, 7.46; N, 5.91.

2-Methylthio-4,5-methylenedioxyaniline boiling at 140°-5° C. at 3.0 mm/Hg

Analysis Calc.: C, 52.44; H, 4.95; N, 7.64. Found: C, 52.33; H, 4.69; N, 7.40.

These two anilines were converted to the corresponding 3-oxobenzothiadiazenes by the procedures of Example 5, 6, 7 and 8 to yield 1-methyl-6,7-diethoxy-1H-1,2,4-benzothiadiazine-3(4H)-one-1-oxide melting at 282°-5° C.

Analysis Calc.: C, 50.69; H, 5.67; N, 9.85. Found: C, 50.67; H, 5.43; N, 9.87.

and 1-Methyl-6,7-methylenedioxy-1H-1,2,4-benzothiadiazine-3(4H)-one-1-oxide melting at 338°-44° C.

Analysis Calc.: C, 45.00; H, 3.36; N, 11.66. Found: C, 45.27; H, 3.44; N, 11.87.

These two oxo compounds were then reacted with phosphorus oxychloride to provide the corresponding 3-chloro compounds which were, in turn, reacted with diethylamine or with 4-(2-furoyl)-piperizine, to yield the following compounds:

1-Methyl-3-diethylamino-6,7-diethoxy-1H-1,2,4-benzothiadiazine-1-oxide hydrochloride melting at 172°-4° C.

Analysis Calc.: C, 51.12; H, 6.97; N, 11.18. Found: C, 50.91; H, 7.16; N, 11.07.

1-Methyl-3-[4-(2-furoyl)-piperazino]-6,7-diethoxy-1H-1,2,4-benzothiadiazine-1-oxide hydrochloride melting at 243°-5° C.

Analysis Calc.: C, 52.22; H, 5.63; N, 11.60. Found: C, 52.14; H, 5.73; N, 11.38.

1-Methyl-3-diethylamino-6,7-methylenedioxy-1H-1,2,4-benzothiadiazine-1-oxide hydrochloride melting at 216°-7° C.

Analysis Calc.: C, 47.06; H, 5.47; N, 12.66. Found: C, 47.33; H, 5.41; N, 12.73.

1-Methyl-3-[4-(2-furoyl)piperazino]-6,7-methylenedioxy-1H-1,2,4-benzothiadiazine-1-oxide hydrochloride melting at 242°-5° C.

Analysis Calc.: C, 49.26; H, 4.36; N, 12.77. Found: C, 49.50; H, 4.44; N, 12.78.

By employing 2,3,4-trimethoxy-6-nitrophenylbromide as a starting material, and following the procedures of the above examples, 1-methyl-3-[4-(2-furoyl)-piperazino]-6,7,8-trimethoxy-1H-1,2,4-benzothiadiazine-1-oxide hydrochloride was prepared. The compound melted at 130°-2° C.

Analysis Calc.: C, 49.53; H, 5.20; N, 11.55. Found: C, 49.30; H, 5.22; N, 11.28.

EXAMPLE 13

Preparation of salts

Salts of the free bases of this invention are prepared by dissolving the free base in ether and adding an equivalent of a suitable non-toxic acid, for example, maleic acid, also in ether. The salt thus formed, as for example the maleate salt, is insoluble in ether and can be isolated by filtration. Alternatively, the amine base can be dissolved in ethanol and an equivalent of the acid, for example, sulfuric acid, added as an ethanolic solution. In this instance, since the salt thus formed is soluble in the reaction mixture, the salt is isolated by evaporation of the solvent in vacuo. Salts which can be formed by the above procedures include, among others, the hydrochloride, hydrobromide, phosphate, hydrogen phosphate, dihydrogen phosphate, acetate, succinate, tartrate, citrate, benzoate, and p-toluene sulfonate salts.

Compounds of this invention are active not only in lowering the blood pressure of normotensive mammals but also in lowering the blood pressure of hypertensive mammals, specifically spontaneously hypertensive rats. Such rats, which are available commercially, are divided into groups of 4 and each group given a predetermined dosage level of the drug under test. Each rat serves as his own control. The blood pressure is measured indirectly by the procedure developed by Terrence T. Yen and co-workers of the Lilly Research Laboratories, Indianapolis, Ind. as follows: the blood pressure in the rat is measured automatically using an inflatable cuff around the rat tail. The cuff is inflated to a pressure of about 300 mm/Hg. and then deflated to a pressure of 0 mm/Hg. over a period of 11 seconds. The blood pressure is recorded automatically. In carrying out the determination, the systolic blood pressure is measured just before administration of the drug and then one hour after. The response is graded on a plus, double plus and triple plus system. The compounds of this invention in general show a statistically significant plus or double plus effect on blood pressure when the drug is administered by the intraperitoneal route at dose levels of about 50 mg./kg. 1-Methyl-3-[4-(2-furoyl)-piperazino]-6,7-dimethoxy-1H-1,2,4-benzothiadiazine-1-oxide is particularly active in this test showing a double plus at a dose level of only 2 mg/kg.

Certain of the compounds of this invention, either of such, or in the form of their pharmaceutically-acceptable addition salts such as the hydrochloride, have limited solubility in water which prevents their adequate testing in normotensive rabbits since the intravenous route is used and there is a limit on the amount of fluid which can be injected into the rabbit. On being tested, such insoluble compounds are not listed as being inactive but are listed as not tested. Their hypotensive activity is then determined with spontaneously hypertensive rats where it is easier to administer insoluble compounds via the intraperitoneal route.

We claim:

1. A compound of the formula:

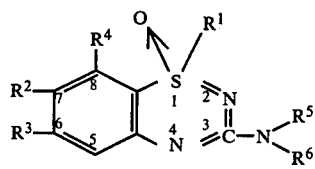

wherein R¹ is C₁–C₃ alkyl,
R⁷ is hydrogen, chloro, bromo, fluoro, methyl, ethyl, methoxy, ethoxy or trifluoromethyl;
R² and R³ when taken singly are methoxy or ethoxy and when taken together are methylene dioxy,
R⁴ is H or methoxy, Ser. No. 783,125
R⁵ and R⁶, when taken together with the nitrogen to which they are attached form a piperidino group

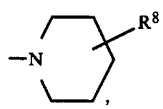

a piperazino group

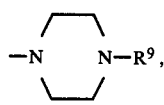

a homopiperzino group

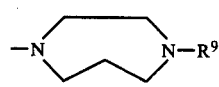

or a 4-hydroxy-4-phenylpiperidino group wherein R⁸ is a substituent in the 3 or 4 position of the piperidine ring chosen from the group consisting of OH, lower alkanoyloxy, lower alkoxy, hydroxy lower alkyl,

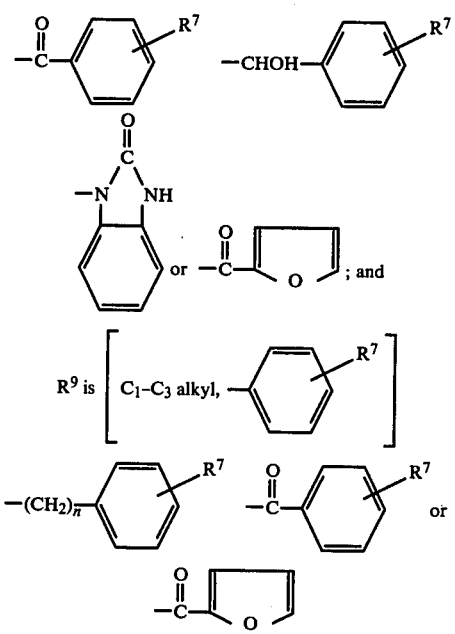

R⁹ is C₁–C₃ alkyl,

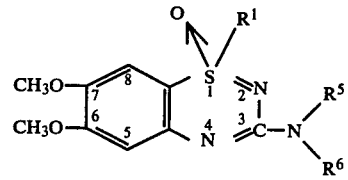

wherein n is 0, 1 or 2, and pharmaceutically-acceptable acid addition salts thereof.

2. A compound of the formula

wherein R¹ is C₁–C₃ alkyl,
R⁷ is hydrogen, chloro, bromo, fluoro, methyl, ethyl, methoxy, ethoxy or trifluoromethyl;
R⁵ and R⁶, when taken together with the nitrogen to which they are attached form a piperidino group

a piperazino group

a homopiperazino group

or a 4-hydroxy-4-phenylpiperidino group wherein R⁸ is a substituent in the 3 or 4 position of the piperidine ring chosen from the group consisting of, OH, lower alkanoyloxy, lower alkoxy, hydroxy lower alkyl,

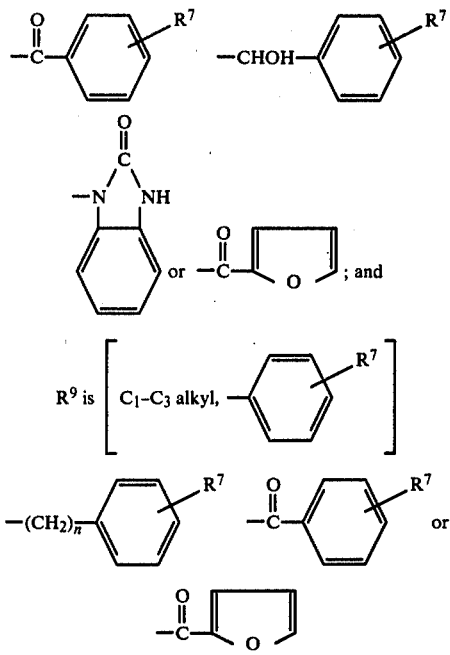

wherein n is 0, 1, or 2, and pharmaceutically-acceptable acid addition salts thereof.

3. A compound of the formula

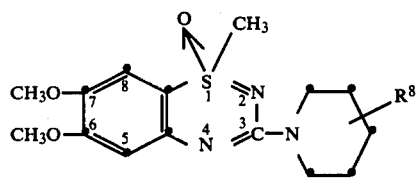

wherein $R^8$ is a substituent in the 3 or 4 position of the piperidine ring chosen from the group consisting of OH, lower alkanoyloxy, lower alkoxy, hydroxy lower alkyl,

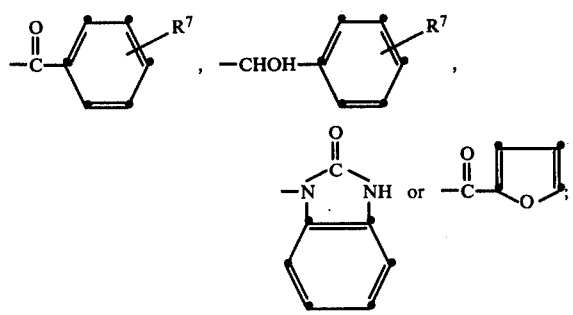

$R^7$ is hydrogen, chloro, bromo, fluoro, methyl, ethyl, methoxy, ethoxy or trifluoromethyl; and pharmaceutically-acceptable acid addition salts thereof.

4. A compound of the formula

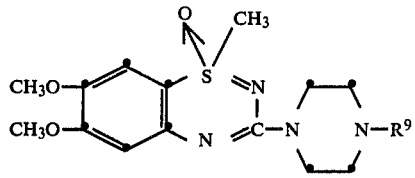

wherein $R^9$ is

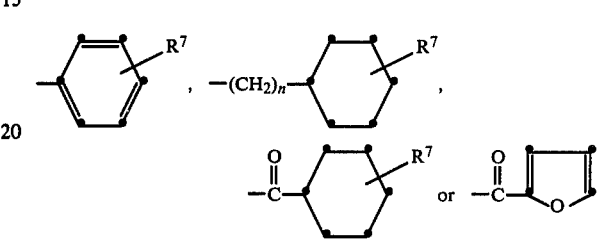

wherein $R^7$ is hydrogen, chloro, bromo, fluoro, methyl, ethyl, methoxy, ethoxy or trifluoromethyl and n is 1 or 2; and pharmaceutically-accetpable acid addition salts thereof.

5. A compound according to claim 1, said compound being 1-methyl-6,7-dimethoxy-3-(4-phenylpiperidino)-1H-1,2,4-benzothiadiazine-1-oxide.

6. A compound according to claim 1, said compound being the hydrochloride of 1-methyl-6,7-dimethoxy-3-(4-phenylpiperidino)-1H-1,2,4-benzothiadiazine-1-oxide.

7. The compound according to claim 1, said compound being 1-methyl-6,7-dimethoxy-3-[4-(α-hydroxybenzyl-piperidino)]-1H-1,2,4-benzothidiazine-1-oxide.

8. A compound according to claim 1, said compound being the hydrochloride salt of 1-methyl-6,7-dimethoxy-3-[4-(α-hydroxybenzylpiperidino)]-1H-1,2,4-benzothiadiazine-1-oxide.

9. A compound according to claim 1, said compound being 1-methyl-6,7-dimethoxy-3-[4-(2-furoyl)-piperazino]-1H-1,2,4-benzothiadiazine-1-oxide.

10. A compound according to claim 1, said compound being 1-methyl-6,7-dimethoxy-3-(4-hydroxypiperidino)-1H-1,2,4-benzothiadiazine-1-oxide.

11. A compound according to claim 1, said compound being The hydrochloride salt of 1-methyl-6,7-dimethoxy-3-[4-(2-furoyl)piperazino]-1H-1,2,4-benzothiadiazine-1-oxide.

12. A compound according to claim 1, said compound being the hydrochloride salt of 1-methyl-6,7-dimethoxy-3-(4-hydroxypiperdino)-1H-1,2,4-benzothiadiazine-1-oxide.

13. The method of reducing blood pressure in a mammal with elevated blood pressure and in need of treatment which comprises administering a hypotensive dose of a compound according to claim 1 sufficient to lower said elevated blood pressure in said hypertensive mammal.

* * * * *

UNITED STATES PATENT AND TRADEMARK OFFICE
CERTIFICATE OF CORRECTION

PATENT NO. : 4,171,361

DATED : October 16, 1979

INVENTOR(S) : Robert D. Dillard et al.

It is certified that error appears in the above—identified patent and that said Letters Patent is hereby corrected as shown below:

Column 8, line 3, after "added", change "on" to -- in --.

Column 13, line 24, at the start of the line, change "51.95" to -- 51.94 --.

Column 14, line 6, change "4-(2-furoyl)-piperizine" to -- 4-(2-furoyl)-piperazine --.

Column 16, lines 15-20, the bracketed formula should be deleted.

Column 17, lines 14-19, the bracketed formula should be deleted.

Signed and Sealed this

Nineteenth Day of February 1980

[SEAL]

Attest:

Attesting Officer

SIDNEY A. DIAMOND

Commissioner of Patents and Trademarks